(12) United States Patent
Wagner et al.

(10) Patent No.: US 6,497,573 B2
(45) Date of Patent: Dec. 24, 2002

(54) COMPOSITE DENTAL ABUTMENT

(75) Inventors: William R. Wagner, Escondido, CA (US); Robert L. Riley, Vista, CA (US); George Tysowsky, Getzville, NY (US)

(73) Assignee: Centerpulse Dental Inc., Carlsbad, CA (US)

( * ) Notice: Subject to any disclaimer, the term of this patent is extended or adjusted under 35 U.S.C. 154(b) by 0 days.

(21) Appl. No.: 09/977,773

(22) Filed: Oct. 15, 2001

(65) Prior Publication Data

US 2002/0076673 A1 Jun. 20, 2002

Related U.S. Application Data

(63) Continuation-in-part of application No. 09/799,224, filed on Mar. 5, 2001, which is a continuation-in-part of application No. 09/126,117, filed on Jul. 30, 1998, now abandoned.

(51) Int. Cl.[7] .................................................. A61C 8/00
(52) U.S. Cl. ....................................................... 433/173
(58) Field of Search ................................. 433/172, 173, 433/174

(56) References Cited

U.S. PATENT DOCUMENTS

| | | | | |
|---|---|---|---|---|
| 5,026,280 A | * | 6/1991 | Dürr et al. | 433/175 |
| 5,125,839 A | * | 6/1992 | Ingber et al. | 433/169 |
| 5,174,755 A | * | 12/1992 | Fukuda | 433/173 |
| 5,447,435 A | * | 9/1995 | Brodbelk | 433/173 |
| 5,662,473 A | * | 9/1997 | Rassoli et al. | 433/172 |
| 5,685,714 A | * | 11/1997 | Beaty et al. | 433/172 |
| 5,759,036 A | * | 6/1998 | Hinds | 433/214 |
| 5,827,062 A | * | 10/1998 | Driskell et al. | 433/173 |
| 5,873,722 A | * | 2/1999 | Lazzara et al. | 433/173 |
| 5,947,732 A | * | 9/1999 | Beaty et al. | 433/172 |
| 5,989,026 A | * | 11/1999 | Rogers et al. | 433/172 |
| 6,152,737 A | * | 11/2000 | Beaty et al. | 433/172 |
| 6,168,435 B1 | * | 1/2001 | Beaty et al. | 433/172 |
| 6,343,930 B1 | * | 2/2002 | Beaty et al. | 433/173 |

* cited by examiner

Primary Examiner—Ralph A. Lewis
(74) Attorney, Agent, or Firm—Philip S. Lyren (57) ABSTRACT

A dental abutment having a metallic core, a shield surrounding an outer surface of the core, and a polymeric cuff surrounding the core and shield, wherein the cuff bonds to a polymeric prosthesis.

10 Claims, 6 Drawing Sheets

COMPOSITE DENTAL ABUTMENT

BACKGROUND

This is a continuation-in-part of U.S. application Ser. No. 09/799,224, filed on Mar. 5, 2001, which is a continuation-in-part of U.S. application Ser. No. 09/126,117, filed on Jul. 30, 1998, invented by William R. Wagner, et al., and entitled "Composite Dental Abutment" and now abandoned.

Figure 1:
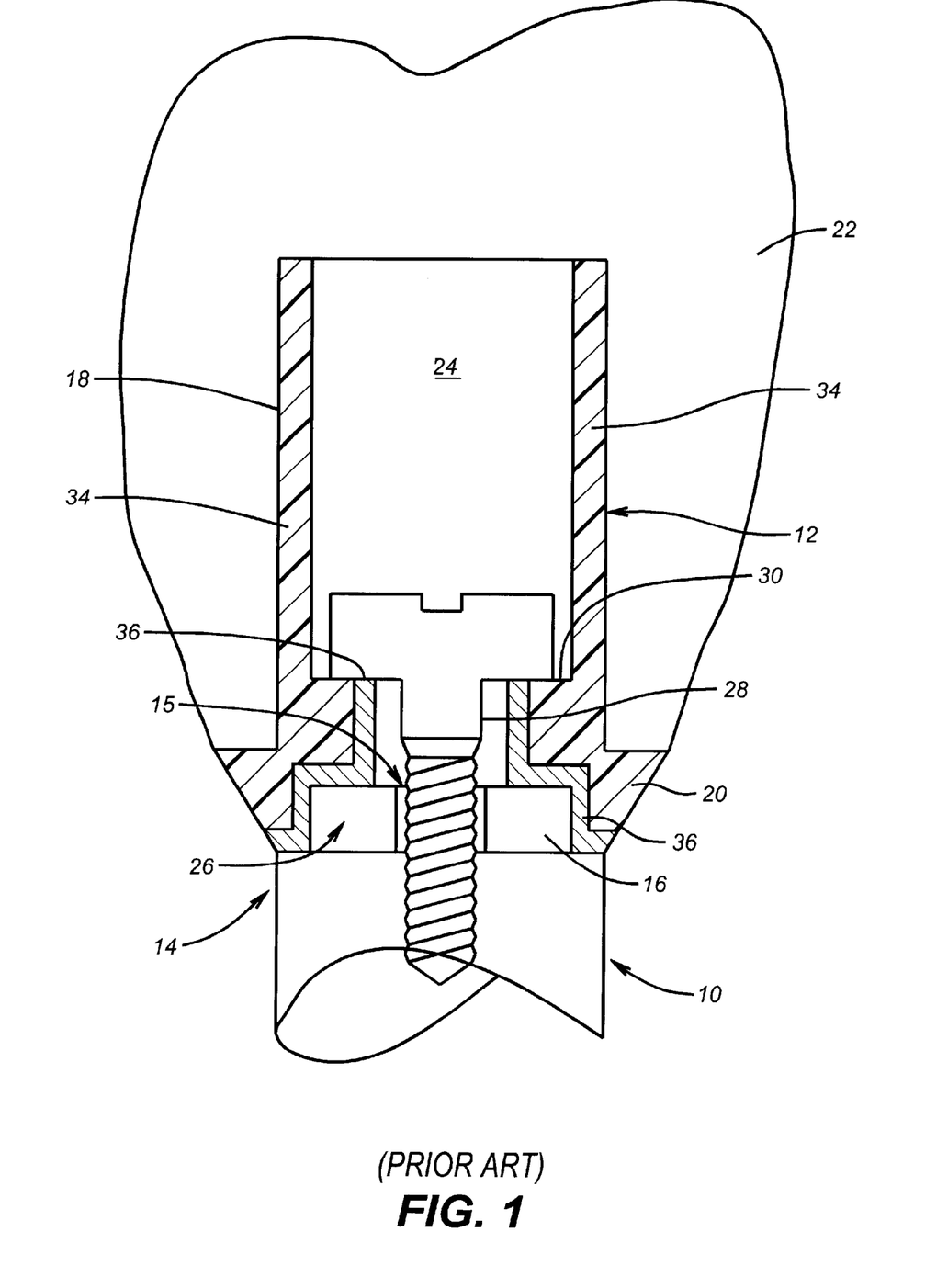
FIG. 1 is a partial cross-sectional view of a prior art dental abutment connected to a prosthesis and implant.

FIG. 1 shows a prior art dental restorative system described in U.S. Pat. No. 5,685,714 entitled "Support Post for Use in Dental Implant System." The system generally includes a dental implant 10 and a support post or abutment 12. The implant is embedded into the jawbone leaving a gingival end 14 exposed through the bone. This gingival end includes a threaded recess 15 and a multi-sided male projection 16 for abutting with the abutment 12.

The abutment has a cylindrical configuration with an elongated upper portion 18 and a lower transgingival portion 20. The abutment serves several functions but generally provides a structure for extending the implant above the gum-line. In this regard, one end of the abutment connects to implant while the other end connects to a prosthesis 22.

A passageway 24 extends through the abutment and provides a recess 26 at the transgingival portion 20 for engaging the projection 16 of the implant. A screw 28 abuts against a shoulder 30 and engages the threaded recess 15 to hold the abutment to the implant. The prosthesis 22 is fabricated around the upper portion and typically connects to the abutment with either a separate screw (not shown) or cement.

Typically, the abutment is made of metal, such as titanium. An entirely metallic abutment, however, can be visible through the prosthesis and can result in a dark, unattractive shadow within the prosthetic structure. In order to alleviate this particular problem, the abutment shown in FIG. 1 is made from two different materials. An outer portion 34 is made from ceramic and an inner portion, shown as an insert 36, is made from titanium or its alloys. The ceramic shields the shadow of the metallic abutment through the prosthesis.

The restorative system shown in FIG. 1 and other prior abutments present numerous disadvantages. The outer portion 34 of the abutment is made of ceramic, typically aluminum oxide. Ceramic, however, is not always a desirable material for use in an abutment. Ceramics, for example, are very brittle and not easily repaired when damaged. If a ceramic component is damaged, for instance chipped, broken, or scratched, it is replaced with a new component. Furthermore, splinted, multiple-tooth ceramic prostheses are very difficult to fabricate because of the hard, brittle nature of the ceramic material. Ceramic components are also difficult to fabricate with precision because of the shrinkage of the ceramic that occurs as the ceramic material is sintered. Further yet, ceramics have a hardness even greater than that of titanium. Once these materials permanently harden, they cannot thereafter be softened and can be re-shaped only by grinding.

The prosthesis 22 is preferably made of porcelain. A porcelain prosthesis bonds well with a ceramic abutment but also is not always a desirable material. Like ceramic, porcelain cannot be easily repaired. If a porcelain prosthesis becomes chipped, for instance, it is replaced and typically not repaired. Additionally, porcelain also permanently hardens once cured. It cannot thereafter be softened and re-shaped. As a further disadvantage, porcelain has a hardness greater than natural teeth. As a result, a porcelain prosthesis will tend to wear an opposing natural tooth during chewing.

The present invention solves the problems discussed above with prior dental restorative systems and provides further advantages.

SUMMARY

The present invention is directed toward a dental restorative system having an abutment formed from two different materials. The abutment includes a metallic core and a polymeric cuff. The core has a cylindrical configuration with an end abutting against a gingival end of a dental implant. The cuff surrounds the outer surface of the core and connects to a prosthesis. The prosthesis is also formed from a polymer and bonds to or abuts the cuff.

The present invention has numerous advantages. For example, both the cuff of the abutment and the prosthesis are made from polymer. These components can be readily repaired if they become chipped, broken, or scratched. Such a repair may occur even after the polymer is hardened and the abutment and prosthesis are placed in the mouth of a patient. Further, the polymeric prosthesis generally will not have a hardness greater than any opposing natural teeth in the patient. As such, the prosthesis will not wear or damage natural teeth as a porcelain prosthesis will. Furthermore, the polymeric cuff can be made to more closely resemble the color of natural teeth than can the traditional metal abutments. As a result, the final restoration will have greatly improved esthetics.

DETAILED DESCRIPTION

Figure 2:
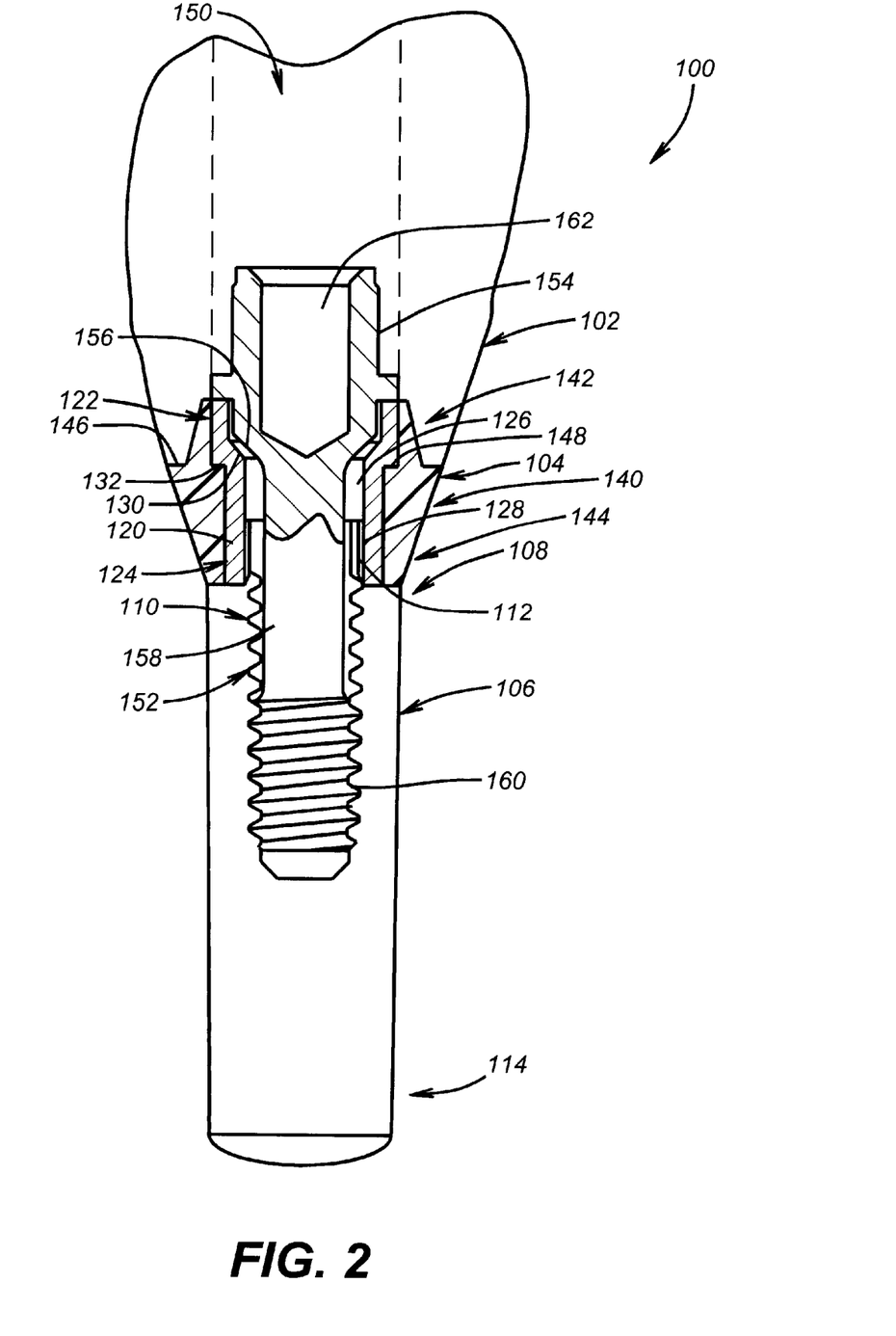
FIG. 2 is a partial cross-sectional view of a dental restorative system according to the present invention.

FIG. 2 shows a dental restorative system 100 that includes a prosthesis 102, an abutment 104, and an implant 106. The abutment and prosthesis are attached together and connected to the implant as illustrated.

Implant 106 has a coronal or gingival end 108 with a threaded bore 110 and a male engaging feature 112 extending upwardly. The coronal end extends downwardly along a cylindrical body to a distal or apical end 114. The engaging feature 112 connects to the abutment and may be a plurality of upwardly extending tines, a polygon, or other type feature known to those skilled in the art. Alternatively, the implant may have female engaging features that correspond with male projections on the abutment core. The implant may be any one of various implants known in the art, such as those manufactured by Sulzer Calcitek Inc. of Carlsbad, Calif.

The abutment 104 has two different and distinct sections formed from two different materials. A core section 120 has a cylindrical configuration and extends from a top portion 122 to a bottom portion 124. A passageway 126 extends centrally through the core. The bottom portion 124 abuts against the coronal end 108 of the implant. Further, this bottom portion may be provided with an engaging feature 128 that engages with the engaging feature 112 to provide an anti-rotational connection between the abutment and implant. The engaging features would have matching configurations to provide the noted anti-rotational connection. For example, if engaging feature 112 is a male hexagonal projection, then engaging feature 128 would be a female hexagonal recess. Of course, the male and female counterparts may be located on either the abutment or implant and numerous configurations of engaging features known to those skilled in the art (such as spline tines, octagons, and other polygons) may be used.

The core also includes a shoulder 130 located along the interior of the passageway 126 at the top portion 122. A corresponding ledge 132 is formed along the exterior surface adjacent the shoulder 130. Preferably, the core is made from a biocompatible metal, such as titanium or its alloys. The metallic core provides strength to the abutment and a framework for connecting the prosthesis to the implant.

A cuff section 140 connects to the exterior surface of the core 120 and, preferably, surrounds the entire exterior surface. The cuff has a somewhat cylindrical configuration and extends from an upper portion 142 to a lower portion 144. The cuff can be shaped around the core to have various configurations, such as a cylindrical or elliptical configuration or an anatomical shape that resembles the cross section of a natural tooth.

As shown in FIG. 2, the lower portion 144 tapers outwardly away from the coronal end 108 of the implant and forms a frusto-conical shape. This tapering continues to a ledge 146 and then transitions to taper inwardly at the upper portion 142. A shoulder 148 is located along the inner surface. This shoulder 148 fits with the mating ledge 132 on the exterior of the core.

The prosthesis 102 is shaped as a natural tooth and includes a passageway 150 that aligns with the passageway 126 of the abutment. A screw 152 passes into these passageways until a head 154 of the screw abuts against the top portion 122 of the core. As shown, the lower portion of the head includes a taper 156 that abuts against the shoulder 130 along the interior of the core. The screw includes a shank 158 extending from the head. This shank has a threaded portion 160 that fits into the coronal end 108 of the implant to engage corresponding threads in threaded bore 110. The screw holds the abutment and attached prosthesis to the implant. The head 154 also includes a recess 162. The recess may be provided to engage a tool (not shown) for tightening and loosening the screw or provided to threadable engage another screw (not shown) to secure the prosthesis.

The cuff 140 of the abutment and the prosthesis 102 are both made from polymeric materials. Various polymers and polymer combinations of polymers are suitable and known to those skilled in the art. Examples of such polymers include: acrylic polymers; fiber, glass, silica, and alumina reinforced polymers; thermosetting and photosensitive polymers; vinylesters; and epoxy type materials. Suitable polymers are sold under trademarks such as Sculpture® or FibreKor® of Jeneric/Pentron, Inc. or Targis® or Vectris® of Ivoclar, Inc.

The polymeric cuff section of the abutment provides numerous advantages. First, a polymeric abutment or prosthesis can be repaired if damaged. Some polymers, for example, can be softened and re-shaped even after they harden. Further, additional polymeric material can be added to the existing structure if a repair is necessary. As another advantage, the polymer in the cuff can bond with the polymer in the prosthesis to form an integrated prosthetic unit. This unit would include the combination of the prosthesis and the abutment.

Figure 3:
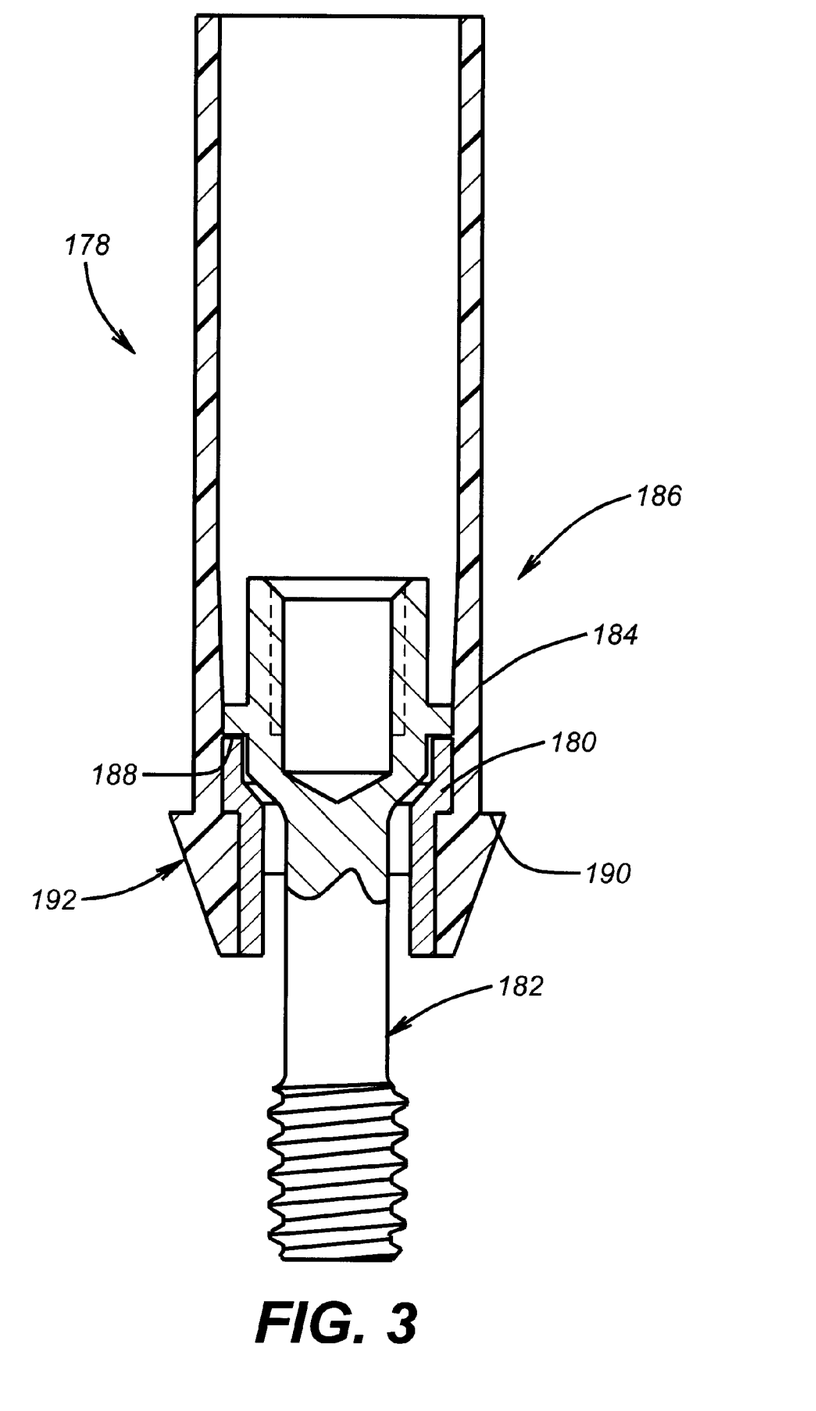
FIG. 3 is cross-sectional view of another embodiment of a dental abutment.

FIG. 3 shows an alternate embodiment for an abutment 178 within the scope of the invention. In the figure, the core 180 and screw 182 are similar to those described in FIG. 2. The polymer cuff 184, however, has an upper portion 186 that extends substantially above the top portion 188 of the core. This upper portion 186 has an elongated cylindrical or elliptical configuration for attaching to a polymeric prosthesis. An optional shelf 190 extends around the exterior of the cuff near the lower portion 192. This shelf provides a support for building the prosthesis directly onto the abutment. Thus, the prosthesis bonds directly to the cuff.

Figure 4:
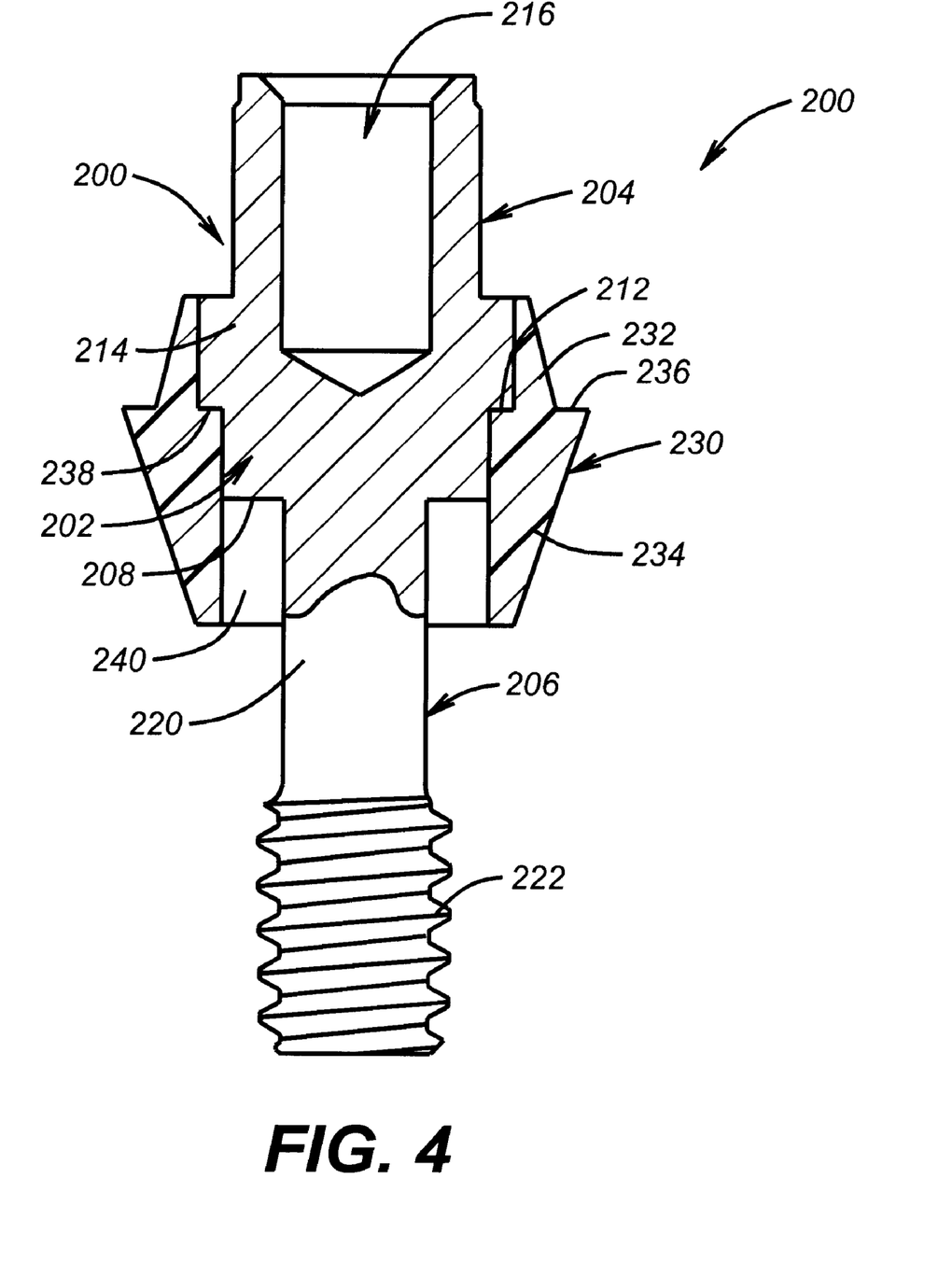
FIG. 4 is a cross-section view of yet another embodiment of a dental abutment.

FIG. 4, another alternate embodiment, shows an abutment 200 that has a single core device 202. This core functions as both the core and screw shown in FIG. 2 Core 202 has a top portion 204 and a bottom portion 206. The top portion includes a bottom surface 208 that abuts against the coronal end of the implant (described in connection with FIG. 2). As shown in FIG. 4, the bottom surface is not configured to engage the anti-rotational features (e.g;, spline tines, polygons) of the implant. Instead, the bottom portion abuts against the gingival end of the implant and is rotatable about this end. This type of connection between the implant and abutment is primarily used in multiple tooth dental restorations.

Still looking to FIG. 4, the top portion 204 includes a ledge 212 located above the bottom surface and further includes a head portion 214 with a recess 216. This recess serves a similar function to the recess described in connection with FIG. 2.

At the other end of the core, the bottom portion includes a shank 220 extending from the top portion. This shank has a threaded portion 222 that fits into the coronal end of the implant to engage a corresponding threaded bore (as shown in FIG. 2).

The abutment 200 also includes a cuff section 230. This cuff surrounds a portion of the exterior surface of the top portion 204. In particular, the outer surface of the upper head portion 214 is not covered. The cuff has a somewhat cylindrical configuration and extends from an upper portion 232 to a lower portion 234. This lower portion tapers outwardly and forms a frusto-conical shape. This tapering continues to a ledge 236 and then transitions to taper inwardly at the upper portion 232. A shoulder 238 is located along the inner surface. This shoulder 238 fits with the mating ledge 212 on the exterior of the core. The cuff could also have other configurations, such as those described in connection with FIG. 2.

In the embodiment shown, the lower portion 234 of the cuff extends below the bottom surface 208 of the core. A cavity 240 thus forms below the bottom surface between the shank 220 and the lower portion. This cavity receives the coronal end of an implant. In the case where the implant does not have an anti-rotational feature, the lower portion 234 may, optionally, not extend below the bottom surface 208 of the core such that no cavity 240 is present.

FIGS. 5A–5D illustrate a method for fabricating a polymeric dental prosthesis on a polymeric abutment. This method, for example, could be used to fabricate a polymeric prosthesis to be used in a single tooth dental restoration.

Figure 5A:
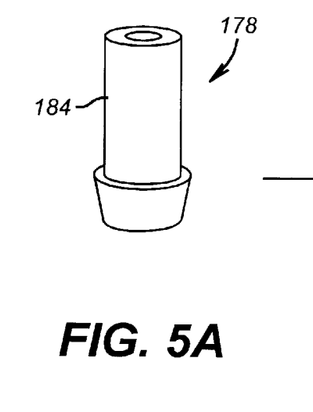
FIGS. 5A–5D are an illustration of a method of fabricating a dental prosthesis on a single dental implant abutment according to the present invention.

FIG. 5A illustrates the abutment 178 described in connection with FIG. 3. The external polymeric cuff 184 surrounds the internal metal core 180 (not visible). The abutment screw 182 has been temporarily removed. Although the abutment described in FIG. 3 is used, it will be appreciated that any abutment within the scope of this invention could be used as well.

Figure 5B:
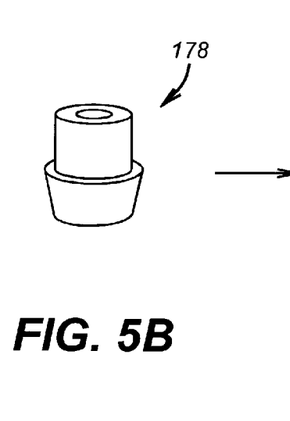

In some instances, the shape of the abutment may need to be modified. Typical modifications include cutting the abutment to a shorter height or grinding the abutment to a new shape. In FIG. 5B, the abutment 178 has been cut to reduce its overall height.

Figure 5C:
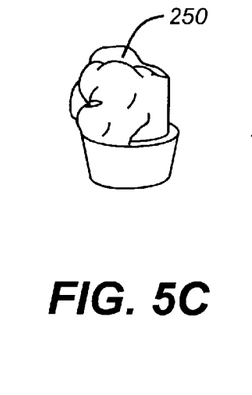

In FIG. 5C, a polymer 250 is being applied around the outer surface of the cuff of the abutment. This polymer is being placed directly onto the cuff of the abutment as the prosthesis is being built. This process continues until the desired size and shape of the prosthesis is obtained. The desired shape can be obtained, for example, by applying and contouring multiple layers of the polymer.

The polymeric material in the cuff 184 and polymer 250 bond directly to each other and create a strong, integrated composition. Various polymers can be used to build the prosthesis. In fact, the composition of the cuff 184 and polymer 250 may be the same material, similar materials, or different materials that are compatible for building dental restorations. Preferably, light or heat is used to catalyze polymerization.

Figure 5D:
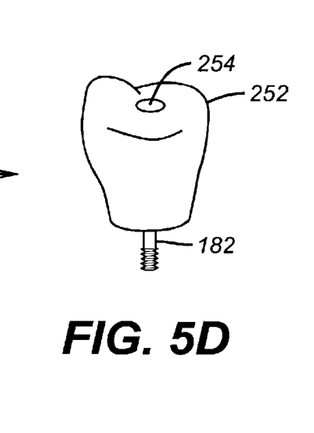

Once the desired size and shape are reached, the prosthesis may be colored to enhance esthetics and more closely match surrounding teeth. In FIG. 5D, the prosthesis 252 is complete and has a size and shape of a natural occurring tooth. The prosthesis 252 includes a bore 254 for passage of the screw 182 described in FIG. 3.

FIGS. 5A–5D illustrate a method for building the prosthesis directly onto the polymeric abutment. It will be appreciated though that other methods may be used to achieve the result of having a polymeric prosthesis on a polymeric abutment. For example, the prosthesis could be formed separately (i.e., not directly on the abutment) using a curable polymeric resin. The prosthesis would be formed with a passageway extending longitudinally through the body of the prosthesis. The prosthesis would be shaped as a natural tooth and then the resin cured. Thereafter, the abutment would be inserted into the passageway. The abutment and prosthesis could be attached using various techniques known to those skilled in the art, such as applying an adhesive or solvent around the cuff of the abutment or along the passageway of the prosthesis. Once the adhesive cured, the prosthesis would be affixed to the implant.

FIGS. 6A–6D illustrate another method for fabricating multiple polymeric dental prosthesis on polymeric abutments. This method, for example, could be used to fabricate prostheses to be used in a multiple tooth, multiple implant-borne dental restorations.

Figure 6A:
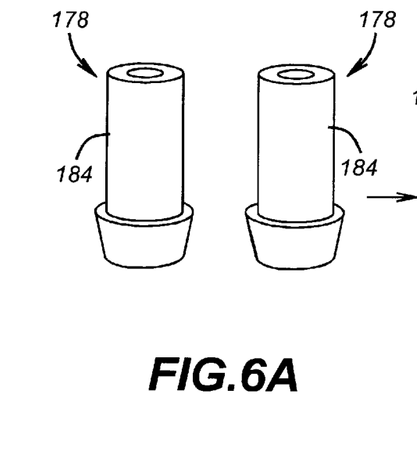
FIGS. 6A–6D are an illustration of a method of fabricating a dental prosthesis on multiple dental implant abutments according to the present invention.

FIG. 6A illustrates two abutments 178 described in connection with FIG. 3. The external polymeric cuff 184 surrounds the internal metal core 180 (not visible). The abutment screw 182 has been temporarily removed. Although the abutment described in FIG. 3 is used, it will be appreciated that any abutment within the scope of this invention could be used as well.

Figure 6B:
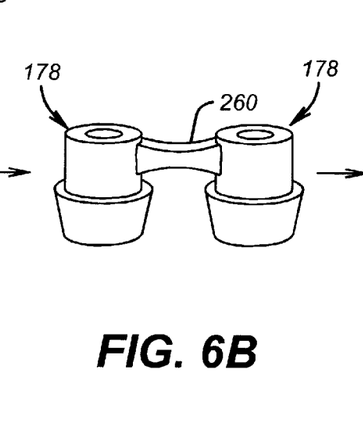

In FIG. 6B, the abutments 178 have been cut to reduce their overall height. Further, they are placed adjacent each other and splinted together. Preferably, the abutments are splinted together with a polymeric framework 260. The framework attaches to the outer surface of the cuff and is preferably made from a reinforced polymer. This polymer preferably would directly bond to the cuffs. As noted, various means may be used (such as light or heat) to catalyze polymerization.

Figure 6C:
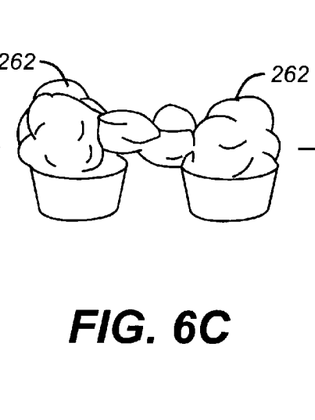

In FIG. 6C, a polymer 262 is being applied around the outer surface of the cuffs and framework. This polymer is being placed directly onto the cuff of the abutment and framework as the prosthesis is being built. This process continues until the desired size and shape of each prosthesis is obtained. The desired shape can be obtained, for example, by applying and contouring multiple layers of the polymer.

The polymeric material in the cuff 184, framework 260, and polymer 262 bond directly to each other and create a strong, integrated composition. Various polymers can be used to build the prosthesis. In fact, the composition of the cuff 184, framework 260, and polymer 262 may be the same material, similar materials, or different materials that are compatible for building dental restorations.

Figure 6D:
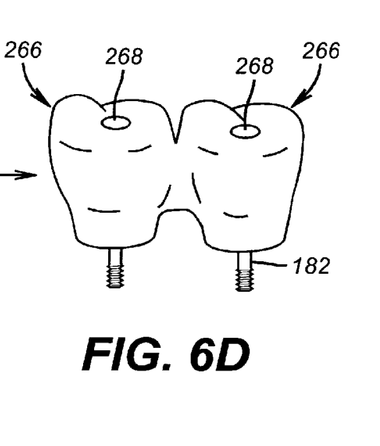

Once the desired size and shape are reached, the multiple prosthesis may be colored to enhance esthetics and more closely match naturally occurring teeth. In FIG. 6D, two prosthesis 266 are complete and have a size and shape of a two natural occurring teeth. Each prosthesis includes a bore 268 for passage of the screw 182 described in FIG. 3.

Figure 7:
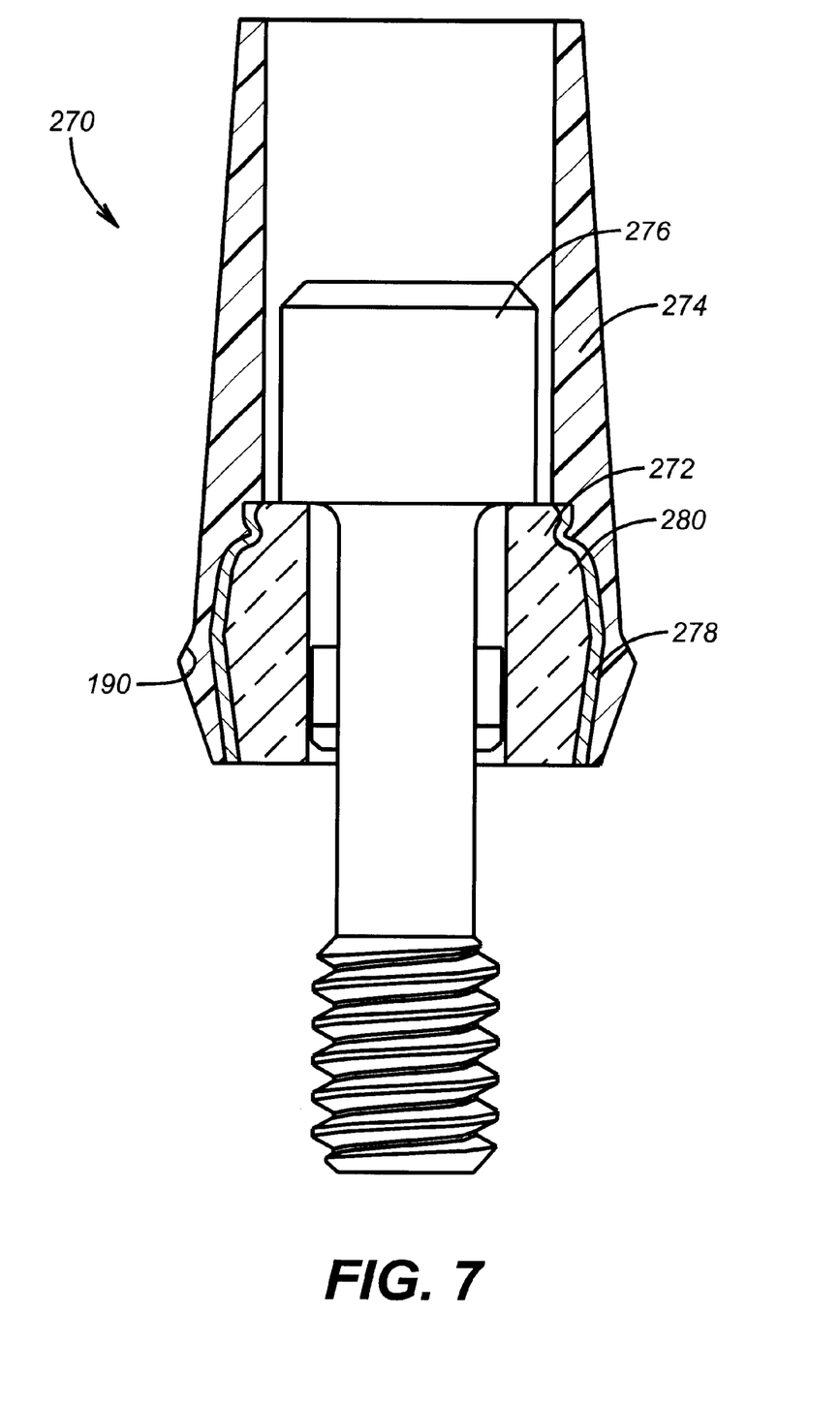
FIG. 7 is a partial cross-sectional view of yet another embodiment of a dental abutment according to the present invention.

FIG. 7 shows another alternate embodiment for an abutment 270 within the scope of the invention. In the figure, the core 272, cuff 274, and screw 276 are similar to those described in FIGS. 2 and 3. In FIG. 7, however, a shield 278 is added. Preferably, this shield extends around the entire outer surface 280 of the core 272 and is formed from an opaque material (as known as opaquers).

One advantage of the shield 278 is that it masks or hides the core and, in particular, any grayish or metallic color of the core. As such, the abutment 270 is esthetic since unsightly colors or shades of the core are not visible through the cuff 274.

Preferably, the opaque material is a mixture of several mono and dimethacrylates activated with light initiators. Pigments may be added to the opaque material to provide a variety of colors to best shield or mask the core.

What is claimed is:

1. A dental abutment, comprising:
    a core formed from metal and having a passageway extending from a top portion to a bottom portion, wherein the bottom portion is adapted to abut against a gingival end of a dental implant;
    a shield extending around the core; and
    a cuff formed from polymer, surrounding the core and the shield, and having a passageway concentric with the passageway of the core.

2. The abutment of claim 1 in which:
    the core is formed from titanium or titanium alloys;
    the cuff is formed from a polymeric material containing one or more of an acrylic polymer, a reinforced polymer, a thermosetting polymer, a photosensitive polymer, a vinylester, or an epoxy; and
    the shield is formed from a mixture of mono and dimethacrylates.

3. The abutment of claim 2 in which the core has an outer surface and the shield surrounds the entire outer surface of the core.

4. The abutment of claim 2 in which the shield is activated with a light initiator.

5. The abutment of claim 1 in which the core has a grayish or metallic color, and the shield is adapted to mask the color of the core.

6. A dental restorative system, comprising:

a dental implant having a coronal end and an apical end;

an abutment having three different regions with each region formed from a different material and including: a core region formed from metal and having a bottom portion for engaging the coronal end of the implant, a shield region formed from an opaquer and positioned around the core, and a cuff region formed from polymer and surrounding the core and shield regions; and a prosthesis formed from polymer and bonded to the cuff region.

7. The dental system of claim 6 in which the cuff is formed from a polymeric material containing one or more of an acrylic polymer, a reinforced polymer, a thermosetting polymer, a photosensitive polymer, a vinylester, or an epoxy; and the shield is formed from a mixture of mono and dimethacrylates.

8. The dental system of claim 6 in which the core includes an inner and outer surface; and the shield surrounds substantially the entire outer surface.

9. A dental prosthetic system, comprising;

a dental prosthesis formed from a polymer and being shaped as a natural tooth; and;

a dental abutment having three different sections: a metallic core, a shield surrounding a portion of the core, and a polymeric cuff surrounding the core and the shield, wherein the cuff is integrally bonded to the prosthesis.

10. The dental prosthetic system of claim 9 in which the polymeric cuff and polymeric prosthesis are formed from substantially the same polymeric ingredients;

the core is formed from titanium or titanium alloys; and the shield is formed from a mixture of mono and dimethacrylates.

* * * * *